(12) United States Patent
Bittman et al.

(10) Patent No.: US 8,277,775 B2
(45) Date of Patent: Oct. 2, 2012

(54) BORON DIPYRROMETHENE DIFLUORO (BODIPY) CONJUGATES

(75) Inventors: Robert Bittman, Roslyn Heights, NY (US); Zaiguo Li, Little Neck, NY (US)

(73) Assignee: The Research Foundation of the City University of New York, New York, NY (US)

( * ) Notice: Subject to any disclaimer, the term of this patent is extended or adjusted under 35 U.S.C. 154(b) by 30 days.

(21) Appl. No.: 12/673,799

(22) PCT Filed: Aug. 15, 2008

(86) PCT No.: PCT/US2008/009792
§ 371 (c)(1),
(2), (4) Date: Dec. 20, 2010

(87) PCT Pub. No.: WO2009/025767
PCT Pub. Date: Feb. 26, 2009

(65) Prior Publication Data
US 2011/0082300 A1    Apr. 7, 2011

Related U.S. Application Data

(60) Provisional application No. 60/956,442, filed on Aug. 17, 2008.

(51) Int. Cl.
*A61B 5/055* (2006.01)
*A61K 31/41* (2006.01)
*A61K 31/69* (2006.01)
*A61K 51/00* (2006.01)
*C07D 249/00* (2006.01)
*C07F 5/04* (2006.01)

(52) U.S. Cl. .......... 424/1.61; 424/9.3; 514/64; 514/277; 544/229; 548/110; 568/2

(58) Field of Classification Search ............... 424/1.61, 424/9.3; 514/64, 277; 544/229; 548/110; 568/2
See application file for complete search history.

(56) References Cited

U.S. PATENT DOCUMENTS
6,476,004 B1    11/2002    Sakai et al.

FOREIGN PATENT DOCUMENTS
WO    2006129688 A1    12/2006
WO    2007069712 A1    6/2007

OTHER PUBLICATIONS

Chiba, et al., J. Immunol., 1998, vol. 160, pp. 5037-5044.*
P. Ettmayer et al., "NBD-labeled derivatives of the immunomodulatory drug FTY720 as tools for metabolism and mode of action studies," Bioorg. Med. Chem. Lett. 16 (2005) 84-87.

* cited by examiner

*Primary Examiner* — Susannah Chung
(74) *Attorney, Agent, or Firm* — Hoffmann & Baron, LLP

(57) ABSTRACT

The present invention relates to FTY720 analogs bearing a boron dipyrromethene difluoro (BODIPY) fluorophore in the alkyl side chain and methods of preparation. The compounds of the present invention can be used in fluorescence spectroscopy and fluorescence microscopy and in chromatography using fluorescence detection.

11 Claims, No Drawings

BORON DIPYRROMETHENE DIFLUORO (BODIPY) CONJUGATES

This invention was supported by the National Institutes of Health, grant number HL-083187. The United States government has certain rights in the invention.

BACKGROUND OF THE INVENTION

Sphingosine 1-phosphate (S1P) mediates numerous biological processes. Accordingly, potential new drug candidates may be specific agonists and antagonists of S1P receptors.

Chemical manipulation of myriocin led to the development of a new immunosuppressive sphingosine analog known as FTY720 (2-amino-2-[2-(4-octylphenylethyl]-1,3-propanediol), which is phosphorylated in vivo and acts as an agonist for several G-protein coupled sphingosine 1-phosphate receptors.

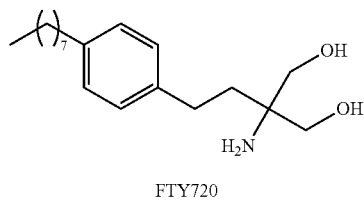

FTY720

The (S)-phosphate of FTY720 is an analog of S1P and is a potent agonist of the S1P-type 1 receptor (and three other S1P receptors), but does not activate the S1P-type 2 receptors on the surface of thymocytes and lymphocytes. FTY720 possesses more potent immunosuppressive activity without inhibiting sphingolipid biosynthesis and host immune defense responses to most infectious agents. FTY720 inhibits lymphocyte trafficking in vivo, promoting sequestration of lymphocytes into lymph nodes and impairing S1P type 1-mediated migration of lymphocytes between secondary lymphoid tissues and the blood, rendering the cells unresponsive to S1P and external signals that direct these cells to sites of inflammation.

FTY720 is a potent inhibitor of several autoimmune diseases such as type 1 diabetes and arthritis. As FTY720 and its (S)-phosphate activate S1P receptors and stimulate various signaling pathways, they appear to have utility for treatment of a variety of pathological conditions, including angiogenesis, inflammation, respiratory distress syndrome, and autoimmune diseases.

Although FTY720 failed to improve efficacy for preventing renal allograft rejection in phase III clinical studies, a different purpose has been found for its potential use. Phase III clinical trials are underway to examine the utility of FTY720 for potential treatment of systemic lupus erythematosus and multiple sclerosis. (S)-FTY720-phosphate stimulated, via induction of ERK1/2 and Akt phosphorylation, the survival of progenitor cells that give rise to myelin-producing mature oligodendrocytes. Therefore, in addition to its immunosuppressive function, FTY720 shows promise as a therapeutic agent in treatment of multiple sclerosis via replenishment of lost oligodendrocytes, thus promoting remyelination.

FTY720 was recently found to enhance pulmonary endothelial cell barrier integrity by a mechanism that appears to be different than that utilized by sphingosine 1-phosphate, which also enhances endothelial cell vascular barrier integrity. FTY720 also has potential therapeutic action in eicosanoid-driven inflammatory disorders.

The exact mechanism of action of FTY720 is under debate. As a result, new derivatives are needed to examine the mechanism of FTY720 in cells, and luminescent derivatives offer the advantage of permitting investigators to monitor intra- and intercellular trafficking of FTY720.

SUMMARY OF THE INVENTION

The invention relates to a molecule having the formula I,

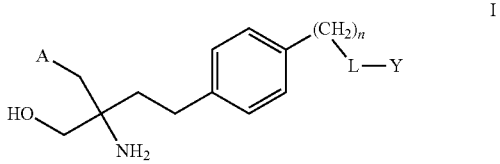

wherein:

n is 1, 2, 3, 4, 5, 6, 7, or 8; and wherein:

L represents a chain comprising 1-20 units, the units selected from the group consisting of: —($CH_2$)—, —CH═CH—, —C≡C—, —NR—, —O—, —S—, —C(O)—, —C(S)—, —C(O)NH—, —NHC(O)—, and a five or six member, carbocyclic or heterocyclic, aromatic or saturated or unsaturated non-aromatic ring, each ring being unsubstituted or substituted with one or more alkyl, aryl, alkoxy, or aryloxy substituent; R represents H, an alkyl group, a carbocyclic aryl group, or a heterocyclic aryl group;

Y represents the following formula:

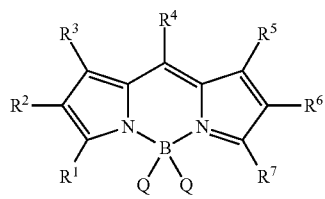

A represents H, OH, alkyl, O-alkyl, a halide, or one of the following structures:

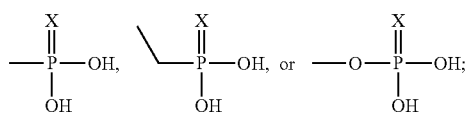

X represents O or S;

$R^1$, $R^2$, $R^3$, $R^4$, $R^5$, $R^6$, and $R^7$ independently represent hydrogen, alkyl, phenyl, alkoxy, or carboalkoxy; or $R^1$ and $R^2$, $R^2$ and $R^3$, $R^5$ and $R^6$, or $R^6$ and $R^7$ represent benzo; provided that one of $R^1$-$R^7$ or Q represents a bond to L;

Q is fluoro, alkyl, alkoxy, aryloxy, or alkynyl;
  alkyl and alkoxy groups are unbranched, saturated, and have 1-4 carbon atoms;
  aryl groups and aryl groups of aryloxy can be either carbocyclic aryl or heterocyclic aryl;
  carbocyclic aryl groups have a total of 6-20 carbon atoms, including carbon atoms of substituents;
  heterocyclic aryl groups have a total of 5-20 carbon atoms, including carbon atoms of substituents;
  carboalkoxy groups are alkyl esters of a carboxylic acid wherein alkyl groups are as defined above;
  each alkyl, aryl, alkoxy, aryloxy, benzo, and carboalkoxy, independently, may be unsubstituted or substituted with one or more substituent;
  alkyl substituents are halo, hydroxyl, amino, or aryl;
  aryl substituents are halo, hydroxyl, amino, alkyl, aryl, nitro, or carboxyl; and
  halo substituents are fluoro or chloro.

In a preferred embodiment, L has one of the following structures:

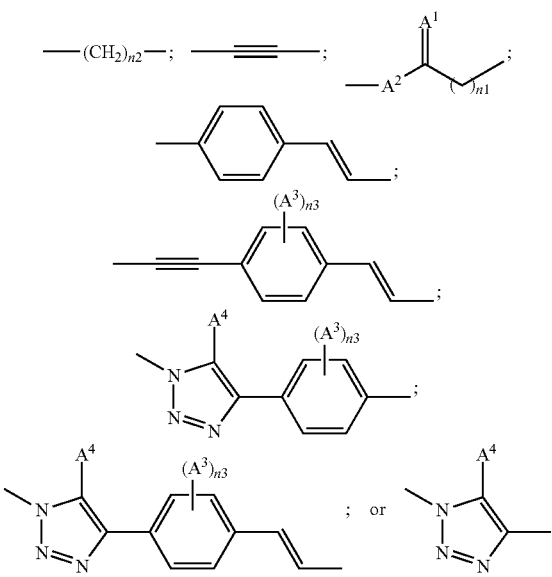

wherein:
n1 is 1, 2, 3, 4, or 5;
n2 is 0, 1, 2, 3, or 4;
n3 is independently 0, 1, 2, 3, or 4;
$A^1$ is O, S or $H_2$;
$A^2$ is O, S, or NH;
$A^3$ is independently alkyl, aryl, alkoxy, or aryloxy; and
$A^4$ is independently hydrogen, alkyl, or aryl.

In a preferred embodiment, $R^1$, $R^4$, $R^7$, or Q represents the bond to L. In another preferred embodiment, A is OH. In another preferred embodiment, L is

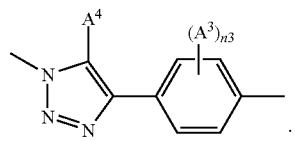

In another preferred embodiment, $R^4$ represents the bond to L and A is OH. In another preferred embodiment, L is —$CH_2$—. In yet another preferred embodiment, $R^4$ represents the bond to L. In another preferred embodiment, L is

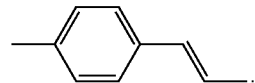

In another preferred embodiment, n is 1 and $R^1$ or $R^7$ represents the bond to L. In yet another preferred embodiment, L represents a chain comprising 1-12 units.

DETAILED DESCRIPTION OF THE INVENTION

It has now been discovered that FTY720 analogs bearing a boron dipyrromethene difluoride (BODIPY) fluorophore in the alkyl side chain may be used to aid in the determination of the mechanism(s) of action of FTY720 within cells.

The present invention is directed to FTY720 analogs bearing a BODIPY fluorophore. The compounds have the formula I:

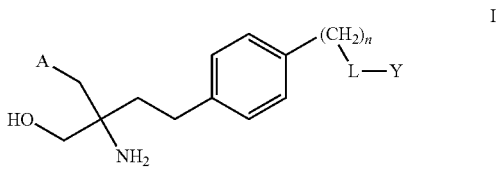

In the above formula, L represents a chain comprising 1-20 units, the units are selected from the group consisting of: —($CH_2$)—, —CH=CH—, —C≡C—, —NR—, —O—, —S—, —C(O)—, —C(S)—, —C(O)NH—, —NHC(O)—, and a five or six member, carbocyclic or heterocyclic, aromatic or saturated or unsaturated non-aromatic ring, each ring being unsubstituted or substituted with one or more alkyl, aryl, alkoxy, or aryloxy substituent. R represents H, an alkyl group, a carbocyclic aryl group, or a heterocyclic aryl group.

In a preferred embodiment, L represents a chain comprising 1-12 units. Preferably, L has one the following structures:

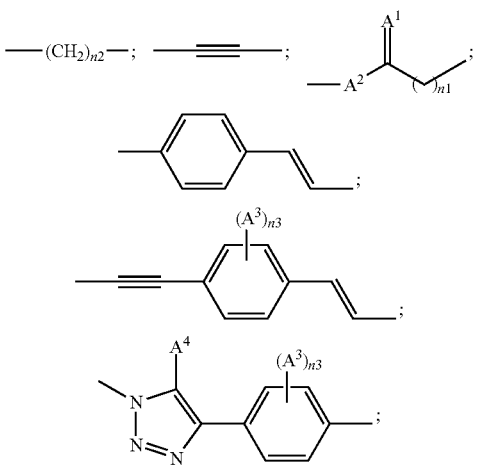

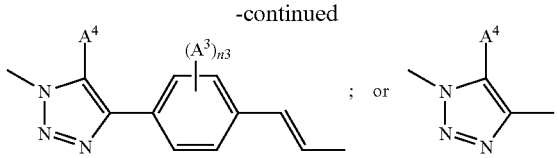

The letter n1 represents 1, 2, 3, 4, or 5. The letter n2 represents 0, 1, 2, 3, or 4. For example, when the linker L is:

—(CH$_2$)$_{n2}$— wherein n2 is 4, the linker is a C$_4$ hydrocarbon chain.

The symbol n3 is independently 0, 1, 2, 3, or 4. For example, the linker may be represented by

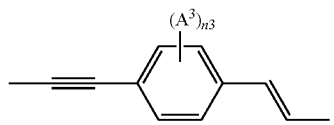

wherein n3 is 0. In this example, the aryl structure contains no A$^3$ substituents.

In the linker, when L is represented by the following structure

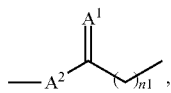

A$^1$ is O, S, or H$_2$ and A$^2$ is O, S, or NH. For example, when A$^1$ and A$^2$ are O, the linker is an ester. When A$^1$ is H$_2$, the linker contains a methylene group. When A$^1$ is O, the linker contains a carboxyl group.

A$^3$ is independently alkyl, aryl, alkoxy, or aryloxy. A$^4$ is independently hydrogen, alkyl, or aryl.

In formula 1, the letter n is 1, 2, 3, 4, 5, 6, 7, or 8.

A represents H, OH, alkyl, O-alkyl, a halide, or one of the following three phosphorus-containing structures:

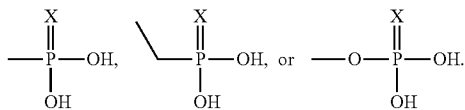

X represents O or S. In a preferred embodiment, A represents OH.

Y represents the following formula:

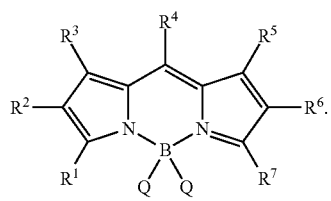

In a preferred embodiment, Y represents a boron dipyrromethene difluoride (BODIPY) fluorophore.

R$^1$, R$^2$, R$^3$, R$^4$, R$^5$, R$^6$, and R$^7$ independently represent hydrogen, alkyl, phenyl, alkoxy, or carboalkoxy; or R$^1$ and R$^2$, R$^2$ and R$^3$, R$^5$ and R$^6$, or R$^6$ and R$^7$ represent benzo, provided that one of R$^1$-R$^7$ or Q represents a bond to L. For example, when R$^1$, R$^3$, and R$^5$ are methyl; R$^6$ and R$^7$ are benzo; and R$^4$ represents a bond to L, the following structure results:

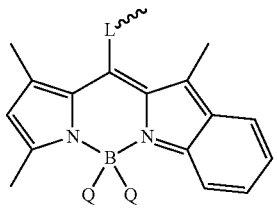

Q is fluoro, alkyl, alkoxy, aryloxy, or alkynyl. In a preferred embodiment, Q is fluoro.

Alkyl and alkyoxy groups are unbranched, saturated, and have 1-4 carbon atoms. Examples of alkyl groups include methyl, ethyl, propyl, and butyl. Examples of alkoxy groups include methoxy, ethoxy, propoxy, and butoxy.

Alkynyl groups are unbranched, unsaturated, and have 1-4 carbon atoms. Examples of alkynyl groups are 1-propynyl, 2-propynyl, 1-butynyl, and 2-butynyl.

Aryl groups and aryl groups of aryloxy can be either carbocyclic aryl or heterocyclic aryl. Carbocyclic aryl groups contain a minimum of six carbon atoms. The maximum number of carbon atoms is twenty, including carbon atoms, if any, of optional substituents and/or fused rings.

Heterocyclic aryl groups contain a minimum of four carbons, except for triazolyl groups which contain two carbons and three nitrogens. The maximum number of carbon atoms is twenty carbon atoms, including carbon atoms, if any, of optional substituents and/or fused rings.

Carbocyclic aryl groups can be unfused or fused. A preferred unfused carbocyclic aryl group is phenyl. Some examples of other fused carbocyclic aryl groups include naphthyl, phenanthryl, and anthracenyl.

Heterocyclic aryl groups contain one or more ring heteroatoms, e.g., nitrogen, oxygen, or sulfur atoms, and may be unfused or fused. Some examples of unfused heterocyclic aryl groups include triazolyl, thiophenyl, furyl, and pyrrolyl. Some examples of fused heterocyclic aryl groups include purinyl, indolyl, benzofuranyl, and benzopyranyl.

A preferred aryloxy is phenoxy. Some examples of other aryloxy groups include naphthyloxy, pyrenyloxy, and furyloxy.

Carboalkoxy groups are alkyl esters of a carboxylic acid wherein alkyl groups are as defined above. Examples of carboalkoxy groups include carbomethoxy, carboethoxy, carbopropoxy, and carbobutoxy.

Each alkyl, aryl, alkoxy, aryloxy, benzo, and carboalkoxy, independently, may be unsubstituted or substituted with one or more substituent. Alkyl substituents are halo, hydroxyl, amino, or aryl. Aryl substituents are halo, hydroxyl, amino, alkyl, aryl, nitro, or carboxyl. Halo substituents are fluoro and chloro. Alkyl and aryl are as defined above.

In the present invention, various parameters are defined (e.g. L, A, A$^1$, A$^2$, n, n1, Y). Within each parameter, more than one element (e.g. number, chemical moieties) are listed. It is to be understood that the instant invention contemplates embodiments in which each element listed under one parameter, may be combined with each and every element listed under any other parameter. For example, $A^1$ is identified above as representing O, S, or $H_2$. $A^2$ is identified above as being O, S, or NH. Each element of $A^1$ (O, S, or $H_2$) can be combined with each and every element of $A^2$ (O, S, or NH). For example, in one embodiment, $A^1$ may be O and $A^2$ may be O. Alternatively, $A^1$ may be $H_2$ and $A^2$ may be S, etc. Similarly, a third parameter is n1, in which the elements are defined as 0, 1, 2, 3, 4, or 5. Each of the above embodiments may be combined with each and every element of n1. For example, in the embodiment wherein $A^1$ is O and $A^2$ is O, n1 may be 2 (or any other number within the elements of n1).

Uses of the Compounds

The mechanism of action of FTY720 and FTY720-phosphate is as yet not elucidated and is likely to involve multiple molecular targets including sphingosine 1-phosphate and anandamide plasma membrane and intracellular receptors, and enzymes involved in sphingolipid metabolism such as sphingosine phosphate lyase and sphingosine kinases. Therefore, fluorescent derivatives of BODIPY-FTY720 and BODIPY-FTY720-phosphate and -phosphonate will allow intracellular tracing and imaging of these targets as well as the movement of the fluorescently labeled compounds between cellular compartments by fluorescence microscopy.

For example, FTY720 is known to promote the survival and differentiation of endogenous oligodendrocyte (myelin-producing) precursor cells, but the mechanism by which FTY720 may spur remyelination remains unclear. See R. P. Coelho, S. G. Payne, R. Bittman, S. Spiegel, and C. Sato-Bigbee, "The Immunomodulator FTY720 Has a Direct Cytoprotective Effect in Oligodendrocyte Progenitors. J. Pharmacol. Exp. Ther. 323, 626-635 (2007). BODIPY-FTY720 will allow an investigation of the identity of the proteins and sphingosine 1-phosphate receptor subtypes with which FTY720 interacts. FTY720 is also an antileukemic, antiviral, and anticancer drug, but its mechanisms of action in these activities have not been elucidated. FTY720 also inhibits the interaction of monocytes with the arterial vessel wall. The fluorescent properties of BODIPY-FTY720 may be used to directly examine atherosclerotic lesions and to study the molecular mechanisms by which FTY720 modulates macrophage function, apoptosis, and tumor suppressor activities. Since BODIPY-FTY720 is phosphorylated efficiently by endogenous sphingosine kinase, the fluorescent product serves as a sphingosine 1-phosphate (S1P) analog with which to assay the activities of enzymes involved in the metabolism of S1P and other long-chain base phosphates, including sphingosine kinase isoenzymes, S1P phosphatase, and S1P lyase. The fluorescently-tagged product can be monitored conveniently and with high sensitivity by chromatographic methods such as HPLC.

Some examples of BODIPY tethered to FTY720 by different linkers include:

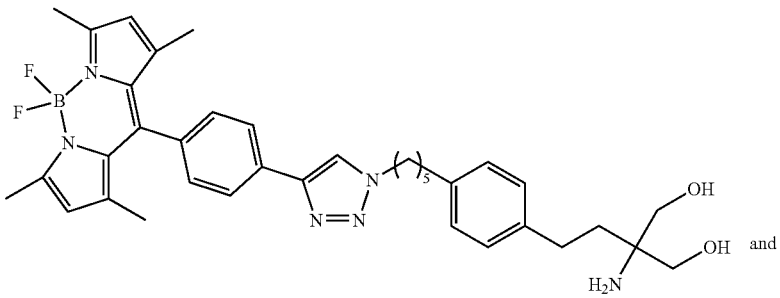

Conjugate 1

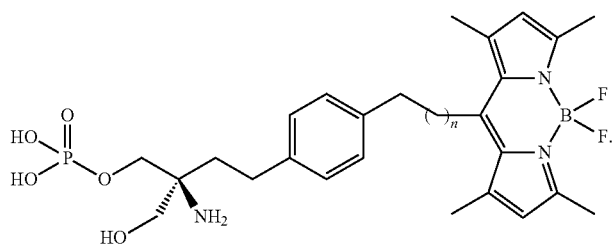

Synthesis of the Compounds

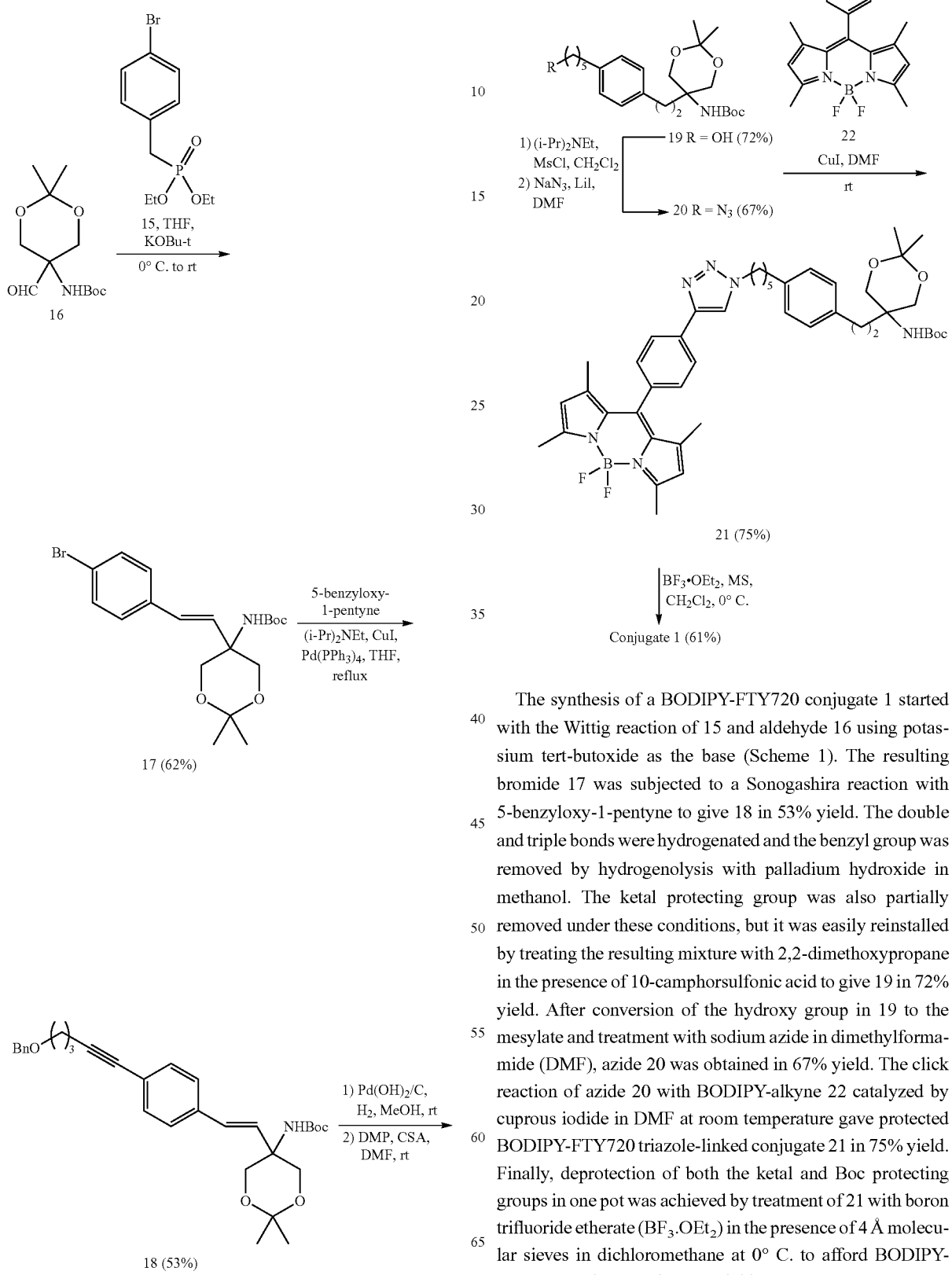

Scheme 1. Synthesis of BODIPY tethered to FTY720

The synthesis of a BODIPY-FTY720 conjugate 1 started with the Wittig reaction of 15 and aldehyde 16 using potassium tert-butoxide as the base (Scheme 1). The resulting bromide 17 was subjected to a Sonogashira reaction with 5-benzyloxy-1-pentyne to give 18 in 53% yield. The double and triple bonds were hydrogenated and the benzyl group was removed by hydrogenolysis with palladium hydroxide in methanol. The ketal protecting group was also partially removed under these conditions, but it was easily reinstalled by treating the resulting mixture with 2,2-dimethoxypropane in the presence of 10-camphorsulfonic acid to give 19 in 72% yield. After conversion of the hydroxy group in 19 to the mesylate and treatment with sodium azide in dimethylformamide (DMF), azide 20 was obtained in 67% yield. The click reaction of azide 20 with BODIPY-alkyne 22 catalyzed by cuprous iodide in DMF at room temperature gave protected BODIPY-FTY720 triazole-linked conjugate 21 in 75% yield. Finally, deprotection of both the ketal and Boc protecting groups in one pot was achieved by treatment of 21 with boron trifluoride etherate ($BF_3 \cdot OEt_2$) in the presence of 4 Å molecular sieves in dichloromethane at 0° C. to afford BODIPY-FTY720 conjugate 1 in 61% yield.

Scheme 2. Synthesis of FTY720 tethered to BODIPY via an amido linkage (Conjugate 2)
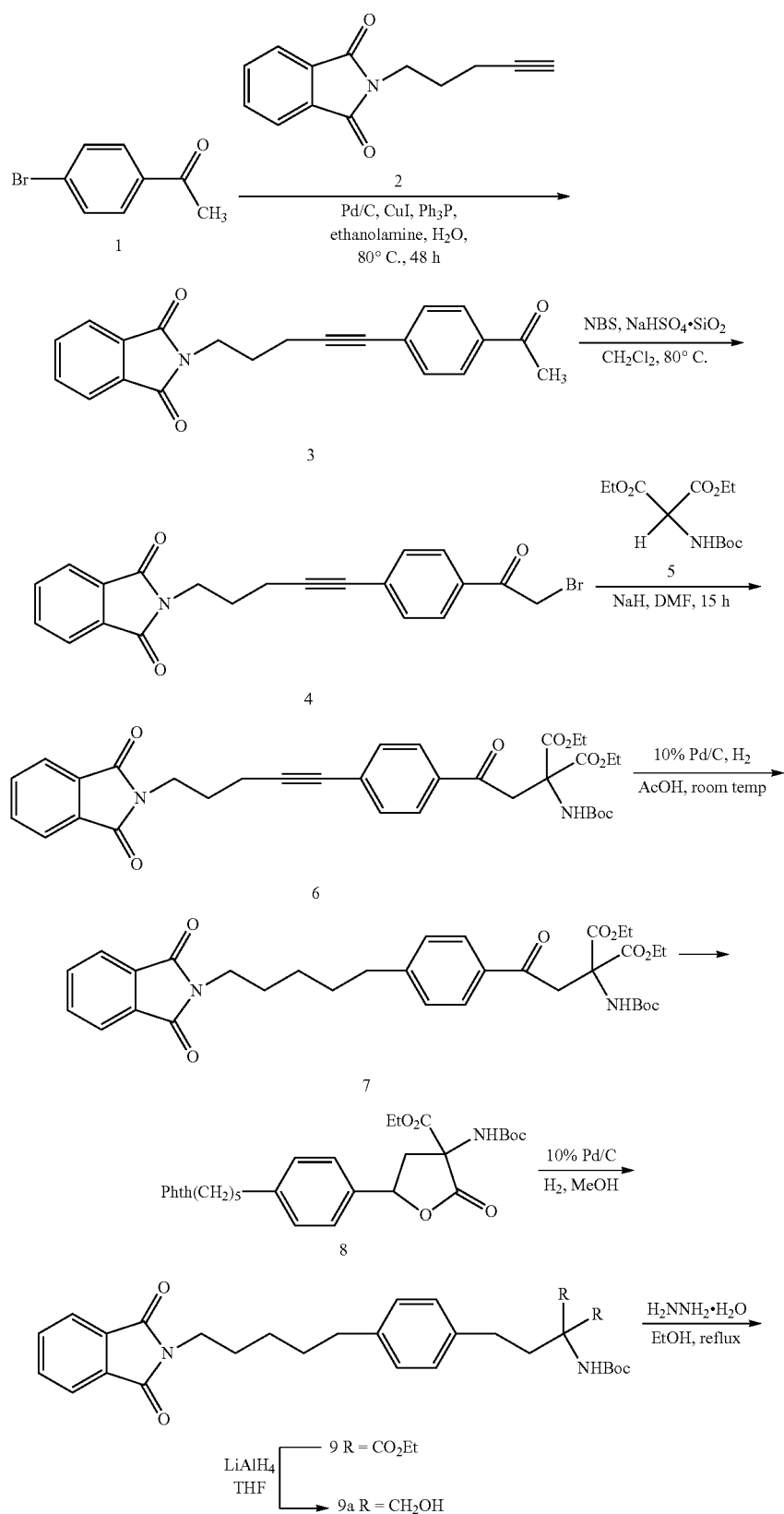

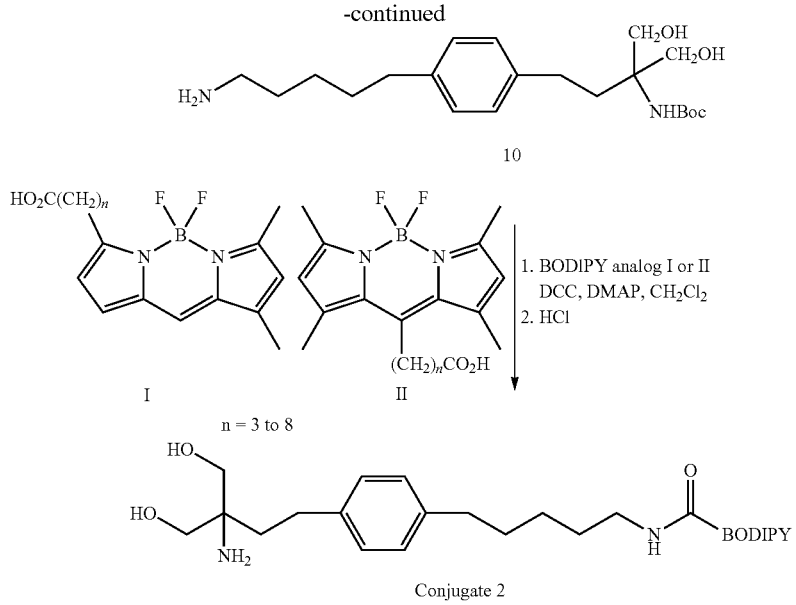

Fluorescently labeled FTY720 compounds are synthesized in ten steps starting from commercially available 4'-bromoacetophenone (1) and N-(4-pentynyl)phthalimide (2) (Scheme 2). The BODIPY fluorescent label is linked to FTY720 by synthesizing the fluorescent label with a carboxyl-containing substituent at either the 5 position or the 8 position of BODIPY (compounds I and II, respectively), and by synthesizing an analog of FTY720 that bears an ω-amino group (compound 10). Acylation of the ω-amino group of compound 10 with the carboxyl group of I and II affords amide-linked conjugate 2. The steps in the synthetic scheme are as follows.

First, a Sonogashira coupling reaction involving the terminal alkyne group of compound 2 with bromo compound 1 is carried out in the presence of cuprous iodide, triphenylphosphine, and palladium on charcoal. The reaction is carried out in water containing 3 equivalents of ethanolamine, with heating at 80° C. for 48 hours, affording compound 3 in 68% yield after purification by silica gel column chromatography (elution with hexanes-ethyl acetate (3:1 v/v).

The next reaction is an α-bromination reaction. Compound 3 is treated with 1.2 equivalents of the brominating agent, N-bromosuccinimide (NBS) in the presence of sodium hydrogen sulfate on silica in dichloromethane, with heating at 80° C. The yield of compound 4 is 48% after purification by silica gel column chromatography (elution with hexanes-ethyl acetate (8:1 v/v); use of more than 1.2 equiv of NBS results in formation of an excessive amount of the undesired α,α-dibromination reaction product.

The third step is the substitution reaction of the anion derived from diethyl 2-[(tert)-butoxycarbonyl)amino]malonate 5 (available commercially) with bromo compound 4 using sodium hydride as the base to deprotonate malonate 5 in dimethylformamide (DMF). The alkylation product, compound 6, is obtained in 80% yield after purification by silica gel column chromatography (elution with hexanes-ethyl acetate (5:1 v/v). Then, the triple bond of compound 6 is hydrogenated using 10% palladium on charcoal as the catalyst and acetic acid as the solvent, with stirring overnight at room temperature. This reaction affords compound 7 in 74% yield.

Compound 7 spontaneously cyclizes to the lactone product 8, which is treated with additional palladium catalyst and reacted with hydrogen in methanol to accomplish the reduction of the α-carbonyl functionality of compound 7 and afford compound 9 in moderate yield (55-60% for the two steps from compound 7 to compound 9).

In the next reaction, the carboethoxy groups of compound 9 are reduced with lithium aluminum hydride in tetrahydrofuran (THF) to provide diol compound 9a in 75% yield. Then, the phthalimido (Phth) group of compound 9a is removed by treating compound 9a with hydrazine monohydrate in ethanol at reflux temperature to provide the ω-amino analog of FTY720 (compound 10) in 82% yield.

The final steps in the preparation of conjugate 2 are the N-acylation of compound 10 with carboxylic acids I or II in the presence of dicyclohexylcarbodiimide (DCC) and 4-(dimethylamino)pyridine (DMAP) in dichloromethane, followed by removal of the Boc group with 1 M HCl in dichloromethane, to provide conjugate 2 in 65-70% yield after purification by silica gel column chromatography. This synthesis allows for the preparation of a variety of different amide-linked BODIPY-FTY720 conjugates.

EXAMPLES

Examples have been set forth below for the purposes of illustration and to describe the best mode of the invention at the present time. The scope of the invention is not to be in any way limited by the examples set forth herein.

Synthesis of BODIPY-FTY720 Conjugate 1

Example 1

Synthesis of 5-tert-Butoxycarbonylamino-5-[(E)-(4-bromophenyl)ethenyl]-2,2-dimethyl-1,3-dioxane (17)

To a solution of aldehyde 16 (0.82 g, 3.14 mmol) and phosphonate 15 (1.45 g, 4.7 mmol) in dry THF (10 mL) was added potassium tert-butoxide (1.58 g, 14.1 mmol) slowly at 0° C. After the mixture was stirred at 0° C. for 3 h and at room temperature overnight, ice-water (20 mL) was added and the suspension was extracted with $CH_2Cl_2$ (3×30 mL). The combined organic layer was washed with water (2×20 mL) and brine (2×20 mL), dried ($Na_2SO_4$), and concentrated under vacuum. The residue was purified by chromatography with gradient elution (hexanes/EtOAc 20:1 to 8:1) to give 17 (0.80 g, 62%). $^1H$ NMR δ 7.37 (d, 2H, J=8.4 Hz), 7.19 (d, 2H, J=8.4 Hz), 6.46 (d, 1H, J=16.4 Hz), 6.21 (d, 1H, J=16.4 Hz), 5.42 (s, 1H), 3.97 (d, 2H, J=11.2 Hz), 3.88 (d, 2H, J=11.2 Hz), 1.50-1.39 (m, 15H); $^{13}C$ NMR δ 154.5, 135.3, 131.2, 129.0, 128.7, 127.6, 121.1, 97.9, 79.1, 65.6, 52.7, 28.1, 27.0, 19.5. HRMS m/z: calcd for $C_{19}H_{27}BrNO_4$ (MH$^+$), 412.1118; found, 412.1120.

Example 2

Synthesis of 5-tert-Butoxycarbonylamino-5-{(E)-[4-(5-benzyloxy-pent-1-ynyl)phenyl]ethenyl}-2,2-dimethyl-1,3-dioxane (18)

To a solution of 17 (0.21 g, 0.51 mmol) and 5-benzyloxy-1-pentyne (133 mg, 0.77 mmol) in N,N-diisopropylethylamine (1 mL, 5.7 mmol) and dry THF (5 mL) were added CuI (9.7 mg, 51 µmol) and tetrakis(triphenylphosphine)palladium(0) (29.5 mg, 25.5 µmol) under nitrogen. The mixture was heated at reflux under nitrogen for one day, and then was cooled to room temperature and filtered through a short pad of silica gel to remove insoluble and very polar components in the mixture. The filtrate was concentrated and dissolved in $CH_2Cl_2$ (50 mL). The solution was washed with water (2×20 mL) and brine (2×20 mL), and dried over $Na_2SO_4$. The solvent was removed under vacuum and the residue was purified by column chromatography (hexanes/EtOAc 20:1 to 6:1) to give 18 (0.14 g, 53%). $^1H$ NMR δ 7.43-7.19 (m, 4H), 6.49 (d, 1H, J=16.4 Hz), 6.21 (d, 1H, J=16.4 Hz), 5.43 (s, 1H), 4.50 (s, 2H), 3.98 (d, 2H, J=11.2 Hz), 3.87 (d, 2H, J=11.2 Hz), 3.59 (t, 2H, J=6.0 Hz), 2.53 (t, 2H, J=6.8 Hz), 1.89 (m, 2H), 1.45 (s, 15H); $^{13}C$ NMR δ 154.4, 138.1, 135.5, 131.3, 129.3, 127.9, 127.2, 127.1, 125.9, 122.8, 97.8, 90.1, 80.6, 79.0, 72.5, 68.3, 65.6, 52.7, 28.5, 28.0, 27.1, 19.3, 15.9. HRMS m/z: calcd for $C_{31}H_{39}NNaO_5$ (MNa$^+$), 528.2720; found, 528.2727.

Example 3

Synthesis of 5-tert-Butoxycarbonylamino-5-{2-[4-(5-hydroxyl-1-pentyl)phenyl]ethyl}-2,2-dimethyl-1,3-dioxane (19)

Palladium hydroxide on carbon (20%) (36 mg, 0.05 mmol) was added to a solution of 18 (0.361 g, 0.71 mmol) in MeOH (8 mL). Hydrogen was bubbled through the suspension with stirring until 18 was completely consumed and converted to a polar substance (monitored by TLC:hexanes/EtOAc 2:1). The mixture was filtered through a short pad of silica gel and concentrated under vacuum. To a solution of the resulting yellow oil in dry DMF (5 mL) were added 2,2-dimethoxypropane (90.5 mg, 0.84 mmol) and camphorsulfonic acid (10 mg, 0.043 mmol). After the mixture was stirred at room temperature for 1 day, it was diluted with saturated aqueous $NaHCO_3$ solution (15 mL) and extracted with $CH_2Cl_2$ (3×20 mL). The combined organic layer was washed sequentially with saturated aqueous $NaHCO_3$ solution (2×20 mL), water (2×20 mL), and brine (20 mL), and was then dried ($Na_2SO_4$). The solvent was removed under vacuum, and the residue was purified by chromatography (hexanes/EtOAc 8:1 to 2:1) to give 19 (217 mg, 72%). $^1H$ NMR δ 7.15-7.05 (m, 4H), 5.09 (s, 1H), 3.89 (d, 2H, J=11.6 Hz), 3.67 (d, 2H, J=11.6 Hz), 3.60 (t, 2H, J=6.8 Hz), 2.60-2.50 (m, 4H), 2.40 (br s, 1H), 1.96 (t, 2H, J=8.0 Hz), 1.65-1.36 (m, 21H); $^{13}C$ NMR δ 154.7, 139.9, 139.0, 128.2, 128.0, 98.2, 79.1, 66.1, 62.4, 51.5, 35.5, 33.5, 32.4, 31.2, 28.4, 28.2, 27.2, 25.3, 19.7. HRMS m/z: calcd for $C_{24}H_{40}NO_5$ (MH$^+$), 422.2901; found, 422.2904.

Example 4

Synthesis of 5-tert-Butoxycarbonylamino-5-{2-[4-(5-azido-1-pentyl)phenyl]ethyl}-2,2-dimethyl-1,3-dioxane (20)

A solution of 19 (168 mg, 0.40 mmol) and N,N-diisopropylethylamine (155 mg, 1.2 mmol) in $CH_2Cl_2$ (10 mL) was cooled to 0° C. Methanesulfonyl chloride (66 mg, 0.60 mmol) was added, and the mixture was stirred at 0° C. for 2 h and then at room temperature overnight. The mixture was washed with saturated aqueous $NaHCO_3$ solution (2×10 mL), water (2×10 mL), and brine (2×10 mL), and then dried ($Na_2SO_4$). After the solvent was removed, the residue was dissolved in dry DMF (5 mL) and lithium iodide (7 mg, 48 µmol) and sodium azide (78 mg, 1.2 mmol) were added. The reaction mixture was stirred at 80° C. for 18 h and then was cooled to room temperature. Water (15 mL) was added, and the suspension was extracted with $CH_2Cl_2$ (3×20 mL). The combined organic layer was washed with water (3×30 mL) and brine (2×20 mL), dried ($Na_2SO_4$), and concentrated under vacuum. The residue was purified by chromatography (hexanes/EtOAc 4:1) to give 20 (119 mg, 67%). $^1H$ NMR δ 7.14-7.04 (m, 4H), 5.02 (s, 1H), 3.89 (d, 2H, J=11.6 Hz), 3.67 (d, 2H, J=11.6 Hz), 3.24 (t, 2H, J=7.2 Hz), 2.60-2.50 (m, 4H), 1.97 (t, 2H, J=8.0 Hz), 1.66-1.56 (m, 4H), 1.47 (s, 9H), 1.43 (s, 3H), 1.41 (s, 3H), 1.40-1.36 (m, 2H); $^{13}C$ NMR δ 154.7, 139.7, 139.2, 128.3, 128.2, 98.2, 79.1, 66.2, 51.6, 51.2, 35.2, 33.5, 30.9, 28.6, 28.5, 28.3, 27.3, 26.2, 19.6. HRMS m/z: calcd for $C_{24}H_{38}N_4NaO_4$ (MNa$^+$), 469.2785; found, 469.2786.

Example 5

Synthesis of 5-tert-Butoxycarbonylamino-5-{2-[4-(5-(4-(4,4-difluoro-1,3,5,7-tetramethyl-3a,4a-diaza-s-indacen-8-yl)phenyl)-1,2,3-triazol-1-yl)pentyl)phenyl]ethyl}-2,2-dimethyl-1,3-dioxane (21)

To a solution of 20 (22.3 mg, 50 µmol) and 22 (17.4 mg, 50 µmol) in dry DMF (1 mL) was added CuI (1 mg, 5 µmol). The mixture was stirred at room temperature until the starting materials are completely consumed (monitored by TLC: hexanes/EtOAc 2:1). Water (5 mL) was added, and the mixture was extracted with $CH_2Cl_2$ (3×10 mL). The combined organic layer was washed with water (2×20 mL) and brine (2×20 mL), and dried over $Na_2SO_4$. After the solvent was removed under vacuum, the residue was purified by chromatography (hexanes/EtOAc 4:1 to 2:1) to afford 21 (29.8 mg, 75%). $^1H$ NMR δ 7.99 (d, 2H, J=8.0 Hz), 7.84 (s, 1H), 7.35 (d, 2H, J=8.0 Hz), 7.13-7.04 (m, 4H), 5.99 (s, 2H), 5.00 (br s, 1H), 4.42 (t, 2H, J=6.8 Hz), 3.90 (d, 2H, J=11.6 Hz), 3.68 (d, 2H, J=11.6 Hz), 2.56 (s, 6H), 2.63-2.49 (m, 4H), 2.03-1.93 (m, 4H), 1.71-1.63 (m, 2H), 1.47 (s, 9H), 1.44 (s, 6H), 1.43 (s, 3H), 1.42 (s, 3H); $^{13}C$ NMR δ 155.5, 154.8, 146.9, 143.0, 141.2, 139.5, 139.4, 134.6, 131.4, 131.3, 128.5, 128.4, 128.3, 126.2, 121.2, 119.8, 98.3, 66.3, 51.6, 50.4, 35.1, 33.6, 30.8, 30.3, 28.6, 28.4, 27.4, 26.1, 19.6, 14.6; $^{19}F$ NMR δ-146.1 (m). HRMS m/z: calcd for $C_{45}H_{57}BF_2N_6NaO_4$ (MNa$^+$), 817.4395; found, 817.4401.

Example 6

Synthesis of 2-Amino-2-{2-[4-(5-(4-(4-(4,4-difluoro-1,3,5,7-tetramethyl-3a,4a-diaza-s-indacen-8-yl)phenyl)-1,2,3-triazol-1-yl)pentyl)phenyl]ethyl}propane-1,3-diol (3)

To a cold solution (0° C.) of 21 (40 mg, 50.3 μmol) in dry $CH_2Cl_2$ (10 mL) were added 4 Å molecular sieves (0.40 g) and $BF_3.OEt_2$ (0.18 g, 1.27 mmol) with vigorous stirring. The mixture was stirred at 0° C., and the reaction was monitored by TLC (hexanes/EtOAc 2:1). On the disappearance of 21 (~5 h), the reaction was quenched by adding saturated aqueous $NaHCO_3$ solution (10 mL). After the mixture was stirred for 30 min, $CH_2Cl_2$ (30 mL) was added. The organic layer was separated and washed with saturated aqueous $NaHCO_3$ solution (20 mL), water (2×20 mL), and brine (2×20 mL). The solution was dried ($Na_2SO_4$) and concentrated under vacuum. The residue was purified by chromatography ($CH_2Cl_2$/MeOH 9:1) to give 3 (20.1 mg, 61%). $^1HNMR$ δ 7.96 (d, 2H, J=8.4 Hz), 7.84 (s, 1H), 7.34 (d, 2H, J=8.4 Hz), 7.11-7.01 (m, 4H), 5.98 (s, 2H), 4.39 (t, 2H, J=7.2 Hz), 3.85-3.57 (m, 4H), 3.56-3.01 (br s, 4H), 2.61-2.51 (m, 4H), 2.55 (s, 6H), 2.00-1.92 (m, 2H), 1.70-1.56 (m, 2H), 1.43 (s, 6H), 1.46-1.05 (m, 4H); $^{13}C$ NMR δ 155.6, 147.0, 143.0, 141.2, 139.8, 138.6, 134.7, 131.4, 128.6, 128.5, 128.3, 126.3, 122.5, 121.3, 119.9, 50.4, 35.1, 30.8, 30.3, 29.7, 29.4, 26.0, 14.6, 14.1; $^{19}F$ NMR δ-146.1 (m). HRMS m/z: calcd for $C_{37}H_{46}BF_2N_6O_2$ (MH$^+$), 655.3737; found, 655.3746.

We claim:
1. A molecule having the formula I,

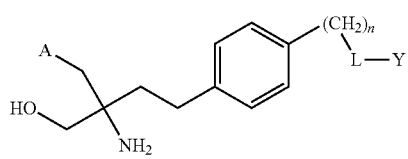

wherein:
n is 1, 2, 3, 4, 5, 6, 7, or 8; and
wherein:
L represents a chain comprising 1-20 units, the units selected from the group consisting of: —($CH_2$)—, —CH=CH—, —C≡C—, —NR—, —O—, —S—, —C(O)—, —C(S)—, —C(O)NH—, —NHC(O)—, and a five or six member, carbocyclic or heterocyclic, aromatic or saturated or unsaturated non-aromatic ring, each ring being unsubstituted or substituted with one or more alkyl, aryl, alkoxy, or aryloxy substituent; R represents H, an alkyl group, a carbocyclic aryl group, or a heterocyclic aryl group;
Y represents the following formula:

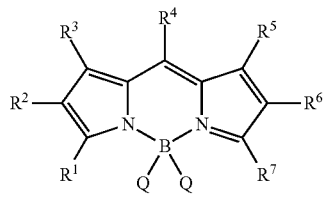

A represents H, OH, alkyl, O-alkyl, a halide, or one of the following structures:

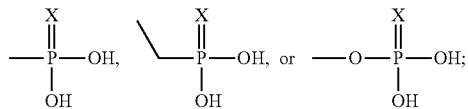

X represents O or S;
$R^1$, $R^2$, $R^3$, $R^4$, $R^5$, $R^6$, and $R^7$ independently represent hydrogen, alkyl, phenyl, alkoxy, or carboalkoxy; or $R^1$ and $R^2$, $R^2$ and $R^3$, $R^5$ and $R^6$, or $R^6$ and $R^7$ represent benzo; provided that one of $R^1$-$R^7$ or Q represents a bond to L;
Q is fluoro, alkyl, alkoxy, aryloxy, or alkynyl;
alkyl and alkoxy groups are unbranched, saturated, and have 1-4 carbon atoms;
aryl groups and aryl groups of aryloxy can be either carbocyclic aryl or heterocyclic aryl;
carbocyclic aryl groups have a total of 6-20 carbon atoms, including carbon atoms of substituents;
heterocyclic aryl groups have a total of 5-20 carbon atoms, including carbon atoms of substituents;
carboalkoxy groups are alkyl esters of a carboxylic acid wherein alkyl groups are as defined above;
each alkyl, aryl, alkoxy, aryloxy, benzo, and carboalkoxy, independently, may be unsubstituted or substituted with one or more substituent;
alkyl substituents are halo, hydroxyl, amino, or aryl;
aryl substituents are halo, hydroxyl, amino, alkyl, aryl, nitro, or carboxyl; and
halo substituents are fluoro or chloro.
2. A molecule according to claim 1, wherein L has one of the following structures:

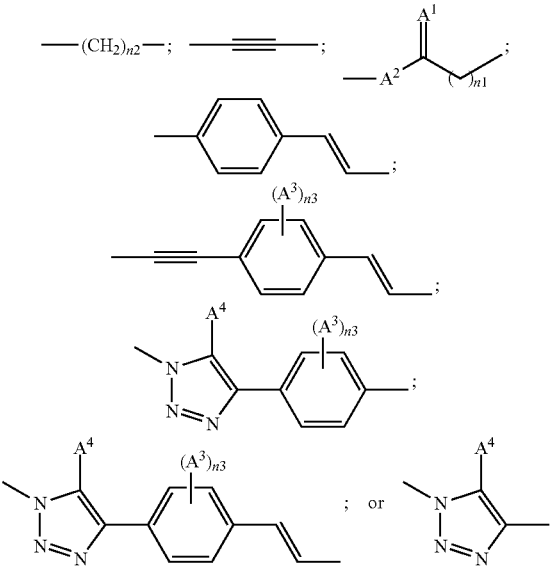

wherein:
n1 is 1, 2, 3, 4, or 5;
n2 is 0, 1, 2, 3, or 4;
n3 is independently 0, 1, 2, 3, or 4;
$A^1$ is O, S or $H_2$;
$A^2$ is O, S, or NH;

$A^3$ is independently alkyl, aryl, alkoxy, or aryloxy; and
$A^4$ is independently hydrogen, alkyl, or aryl.

3. A molecule according to claim 1, wherein $R^1$, $R^4$, $R^7$, or Q represents the bond to L.

4. A molecule according to claim 1, wherein A is OH.

5. A molecule according to claim 2, wherein L is

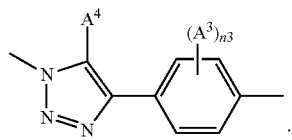

6. A molecule according to claim 5, wherein $R^4$ represents the bond to L and A is OH.

7. A molecule according to claim 1, wherein L is —$CH_2$—.

8. A molecule according to claim 7, wherein $R^4$ represents the bond to L.

9. A molecule according to claim 2, wherein L is

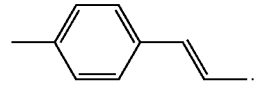

10. A molecule according to claim 9, wherein n is 1 and $R^1$ or $R^7$ represents the bond to L.

11. A molecule according to claim 1, wherein L represents a chain comprising 1-12 units.

* * * * *

UNITED STATES PATENT AND TRADEMARK OFFICE
CERTIFICATE OF CORRECTION

PATENT NO. : 8,277,775 B2
APPLICATION NO. : 12/673799
DATED : October 2, 2012
INVENTOR(S) : Bittman et al.

It is certified that error appears in the above-identified patent and that said Letters Patent is hereby corrected as shown below:

In the Specification

Column 14, line 38

Now reads: "co-amino"

Should read: -- ω-amino --.

Signed and Sealed this
Seventeenth Day of September, 2013

Teresa Stanek Rea
*Deputy Director of the United States Patent and Trademark Office*